United States Patent [19]

Briggs

[11] Patent Number: 4,950,273
[45] Date of Patent: Aug. 21, 1990

[54] CABLE ACTION INSTRUMENT

[76] Inventor: Jeffrey M. Briggs, 48 Hemlock St., Newton, N.J. 07860

[21] Appl. No.: 313,172

[22] Filed: Feb. 21, 1989

Related U.S. Application Data

[63] Continuation-in-part of Ser. No. 112,464, Oct. 26, 1987, abandoned.

[51] Int. Cl.$^5$ ...................... A61B 17/28; A61B 17/32
[52] U.S. Cl. ..................................... 606/113; 606/174;
606/205; 30/251; 181/177.75
[58] Field of Search ............... 606/113, 170, 174, 205;
128/751; 30/177, 296 R, 250, 251; 81/177.75,
57.43; 604/22

[56] References Cited

U.S. PATENT DOCUMENTS

| | | |
|---|---|---|
| 723,629 | 3/1903 | Wiles . |
| 1,754,806 | 4/1930 | Stevenson . |
| 1,869,295 | 7/1932 | Atterbury . |
| 2,512,334 | 6/1950 | Johnson . |
| 2,526,105 | 10/1950 | Adams . |
| 2,579,584 | 12/1951 | Kachelhoffer . |
| 2,994,954 | 8/1961 | Thompson . |
| 3,955,578 | 5/1976 | Chamness et al. . |
| 3,964,468 | 6/1976 | Schulz . |
| 4,254,549 | 3/1981 | McMullin . |
| 4,458,418 | 7/1984 | McSmith et al. . |
| 4,472,878 | 9/1984 | Miller . |
| 4,485,817 | 12/1984 | Swiggert . |
| 4,493,572 | 11/1984 | Schoolman . |

FOREIGN PATENT DOCUMENTS 192346 3/1967 U.S.S.R. .
439303 12/1935 United Kingdom .

*Primary Examiner*—Michael H. Thaler
*Attorney, Agent, or Firm*—Venable, Baetjer, Howard & Civiletti

[57] ABSTRACT

A cable action instrument for surgery and other uses comprises a control end, a reaction end, and an angle adjustment section connecting the control end and the reaction end. A flexible control cable extends between the control end and the reaction end and allows a force to be transmitted from the control end to the reaction end so that a desired function may be performed at an instrument tip. The instrument may be bent into an unlimited number of configurations and is easily disassembled and reassembled.

8 Claims, 6 Drawing Sheets

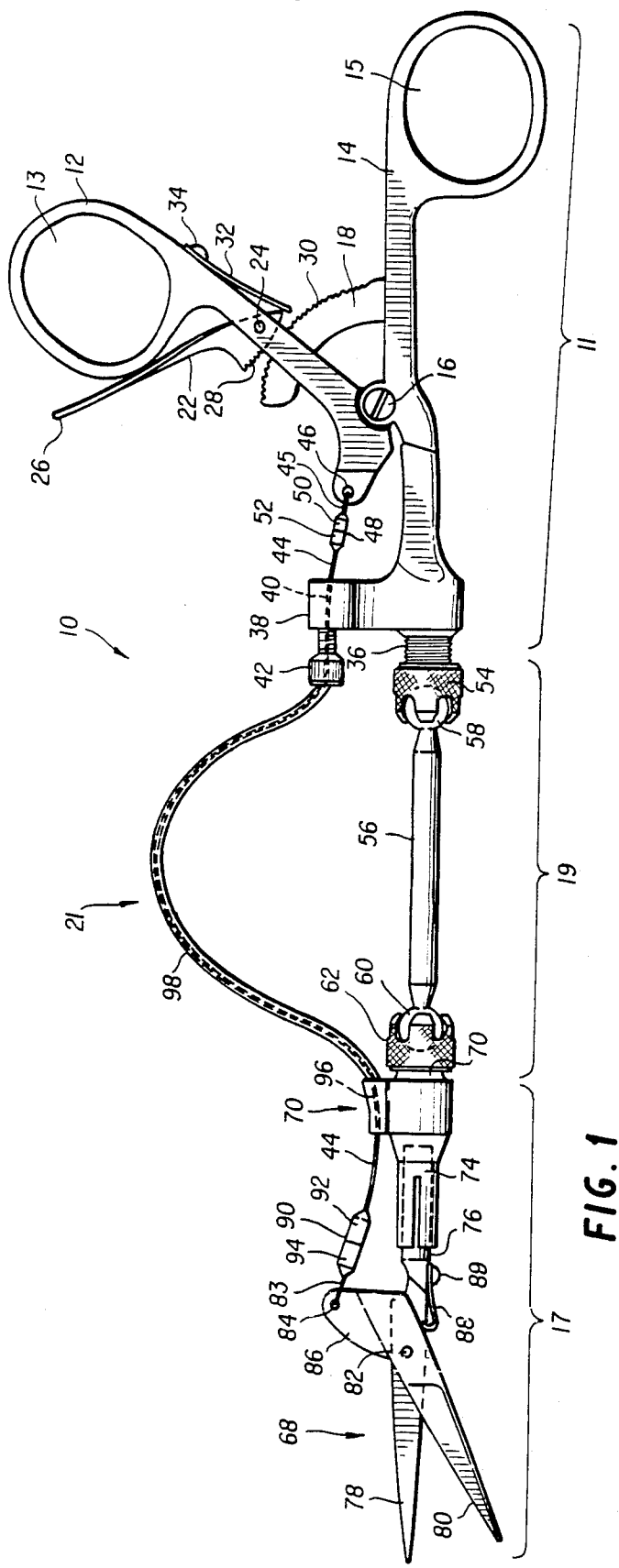
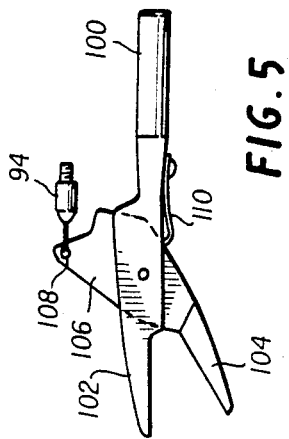
FIG. 1
FIG. 5

CABLE ACTION INSTRUMENT

RELATED APPLICATIONS

This is a continuation-in-part of U.S. patent application Ser. No. 112,464, filed Oct. 26, 1987, now abandoned.

BACKGROUND OF THE INVENTION

Most surgical and other types of instruments are rather rigid and unbendable. These characteristics allow the operator of the instrument excellent control, but sometimes hinder or eliminate the possibility of using the instrument to perform its function at a site which is difficult to reach due to unusual angular entry to the site. Surgeons, dentists and model-makers in particular must often contend with unusual angular entry into the areas in which they must operate. The need for a more flexible instrument is clear.

A further drawback of current surgical and other types of instruments is their unitary construction. If one part of an instrument becomes damaged or unworkable, other than a replaceable part such as a blade, the entire instrument must often be replaced. Thus, a multitude of similar instruments must be kept in stock. An instrument which has interchangeable working ends or tips would eliminate the need for keeping so many similar instruments in stock. Also, an instrument which could be easily disassembled and reassembled would permit the use of replacement parts, ease cleaning and repair processes, and make storage of the instrument more economical. Furthermore, the length of an instrument can be easily varied with replaceable parts.

SUMMARY OF THE INVENTION

The present invention is directed to a cable action instrument comprising a control end, a reaction end and an intermediate angle adjustment section connecting the two ends. A flexible control cable extends from the control end to the reaction and allows a transfer of force from the control end to the reaction end. The control end comprises a cable control lever pivotably connected to a control lever handle, while the reaction end comprises an attachable instrument tip. The angle adjustment section comprises two universal joints joined by a connecting bar. Attachable instrument tips used on the cable action instrument may include a scissors tip, a hemostat tip, and a forceps tip.

The cable action instrument is flexible to allow for operation in an unlimited number of positions. The instrument is also capable of extensive disassembly, which permits easier exchange of parts such as instrument tips, easier cleaning and repair, easier and more economical storage and transport, and easier adjustment of the length of the instrument. Partial disassembly of the instrument by removal of the angle adjustment section also provides a tool useful for work in areas more remote from the control end.

A modified cable action instrument has a snare wire tip on the reaction end and a finger slide to control the cable movement. An optical fiber may also be used in order to provide illumination at the instrument tip.

BRIEF DESCRIPTION OF THE DRAWINGS

The various objects, advantages and novel features of the invention will be more readily appreciated from the following detailed description when read in conjunction with the appended drawings, in which:

FIG. 1 is a side view of a cable action instrument constructed in accordance with the present invention;

FIG. 5 is a side view of a modified instrument tip;

Throughout the drawings, like reference numerals are used to designate like parts and components.

DETAILED DESCRIPTION OF THE INVENTION

Figure 2:
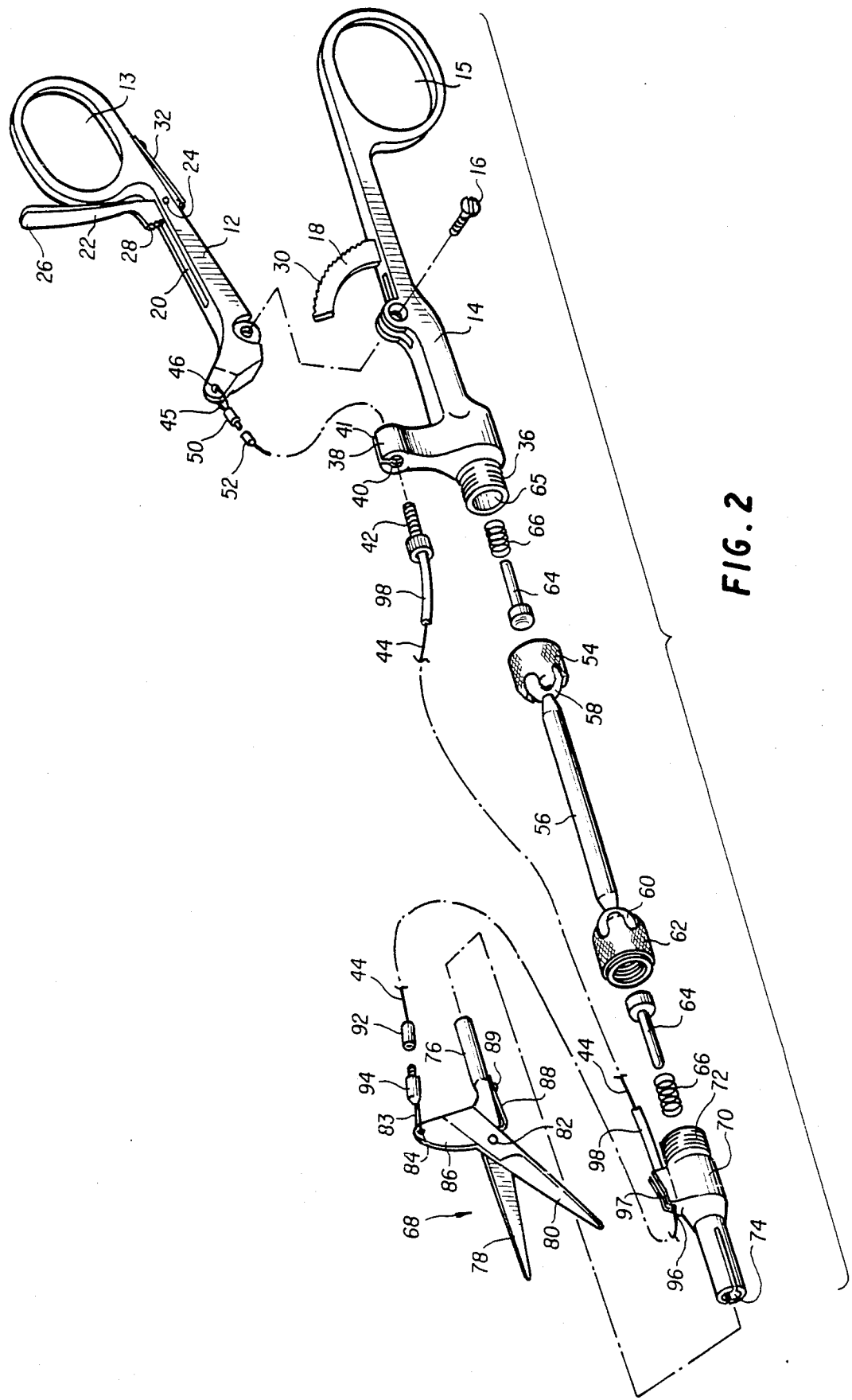
FIG. 2 is an exploded view of the instrument shown in FIG. 1.

A cable action instrument 10 constructed in accordance with the present invention is illustrated in FIGS. 1-4. The instrument 10 comprises a control end 11, a reaction end 17, an angle adjustment section 19 which connects the control end to the reaction end, and a flexible control cable assembly 21 extending between the control end and the reaction end. The angle adjustment section 19 allows for flexibility, bendability and adaptability of the instrument 10. The control cable assembly 21 permits the transfer of force from the control end 11 to complete a desired manipulation or movement at the reaction end 17 of the instrument.

FIG. 1 shows the cable action instrument 10 from a side view in an unbent position. The control end 11 of the instrument 10 includes a cable control lever 12 and a control lever handle 14 as its two major component parts. The cable control lever 12 and the control lever handle 14 are pivotally connected to one another by a threaded screw 16. At one end of the cable control lever 12 is an aperture 13. A similar aperture 15 is located at an end of the control lever handle 14. The apertures 13, 15 permit the insertion of the instrument operator's index finger and thumb, respectively, in order to control the movement of the cable control lever 12. The movement of the cable control lever 12 toward and away from the control lever handle 14 determines the resultant actions of the instrument 10 and its reaction end 17.

When the instrument 10 is being used, the screw 16 permits the user to move the cable control lever 12 toward the control lever handle 14 by the application of a squeezing force between the two. Conversely, the screw 16 also permits movement of the lever 12 and handle 14 away from each other with the application of a separating force. The range of motion of the cable control lever 12 relative to the control lever handle 14 extends from a position in which the lever 12 and handle 14 are immediately adjacent to and in contact with one another, to a position in which the lever 12 and handle 14 are separated by approximately 75°. The latter position is illustrated in FIG. 1.

Figure 3:
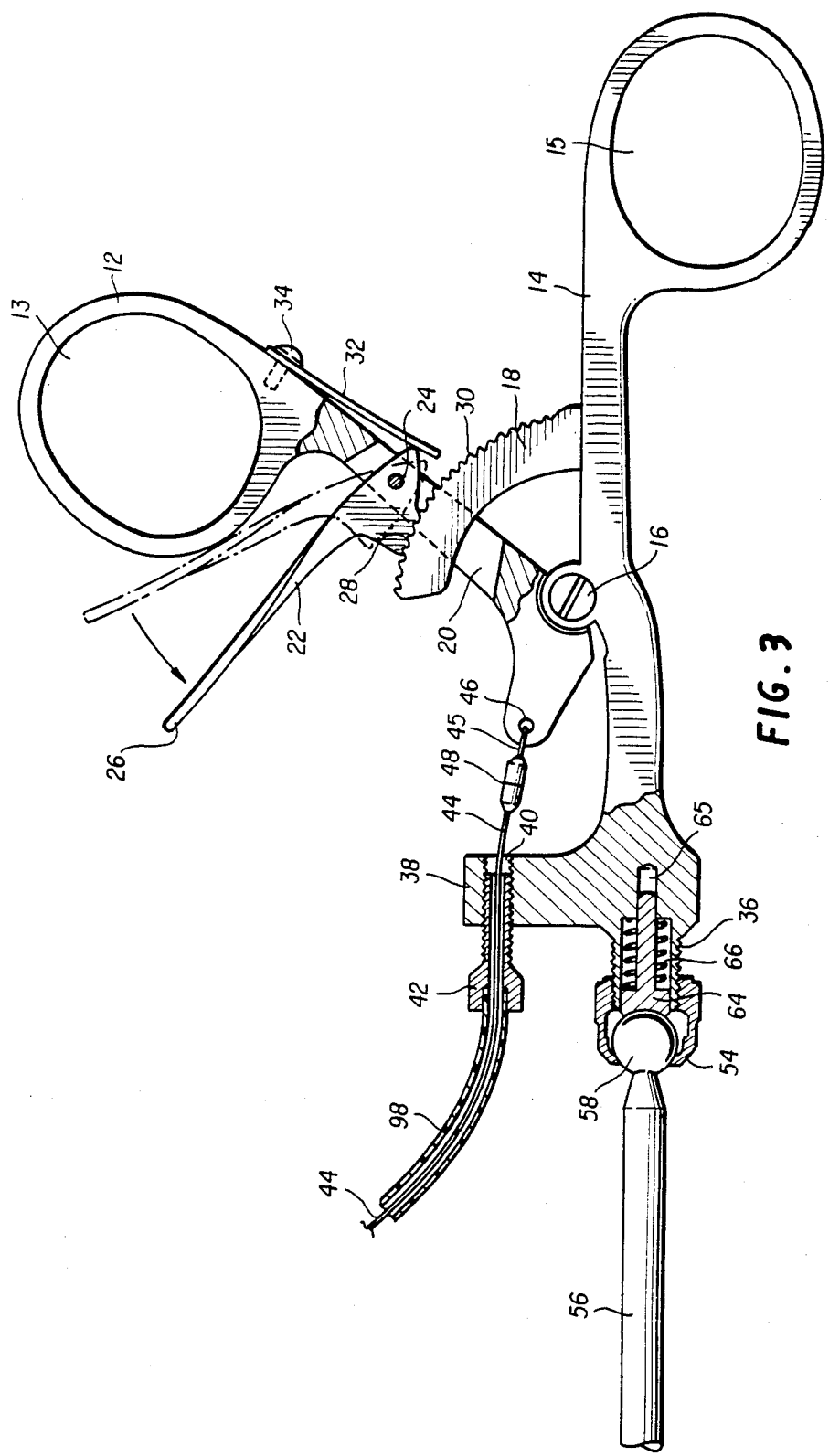
FIG. 3 is a partial sectional view of the control end portion of the instrument.

Attached to the control lever handle 14 is an arcuate ratchet bar 18 which extends in the direction of the cable control lever 12 and is formed with teeth or serrations 30 on its outer arcuate edge. The ratchet bar 18 passes through a slot 20 located in the cable control lever 12, as illustrated in the sectional view of FIG. 3. A ratchet lever 22 is pivotally attached to the cable control lever 12 by means of a pivot pin 24. The ratchet lever 22 includes a control end 26 which is positioned so as to be easily reached and controlled by a finger of the instrument user, and a serrated ratchet engaging end 28 which is positioned in confronting relationship with the serrated edge of the ratchet bar 18. As illustrated in FIG. 3, the counterclockwise pivoting of the ratchet lever 22 by the user results in the engagement of the ratchet engaging end 28 with the ratchet bar teeth 30. In this condition, the cable control lever 12 is held against counterclockwise movement and cannot be further separated from the control lever handle 14; however, due to the angle of the serrations 28, 30, the cable control lever 12 can be moved in a clockwise direction toward the control lever handle 14. Disengagement of the ratchet engaging end 28 from the ratchet bar teeth 30 permits further separation of the cable control lever 12 and the control lever handle 14. This disengagement is affected by pivoting the ratchet lever 22 in a clockwise direction until it assumes the position shown in FIG. 1.

Although the ratchet lever 22 may be allowed to pivot freely if desired, the illustrated embodiment makes use of a leaf spring 32 to create resistance to the pivoting motion of the ratchet lever 22. The leaf spring 32 is attached to the cable control lever 12 by means of a retaining screw 34. The pressure of the leaf spring 32 produces a detent action in the ratchet lever 22, so that the lever tends to remain in the fully engaged position or in the fully released position until it is moved by the user's finger pressure.

The end 36 of the control lever handle 14 which is opposite to and furthest away from the aperture 15 is formed with screw threads as shown in FIG. 2. Intermediate the threaded end 36 and the aperture 15 of the control lever handle 14, but closer to the threaded end 36, is an upstanding shoulder 38. The shoulder 38 is formed with an axial bore which receives an internally threaded bore 40. There is also a slit 41 which extends along the top of shoulder 38 and intersects bore 40. The bore 40 accommodates a cable tension adjustment screw 42. A cable 44 passes through the cable tension adjustment screw 42 and forms a closed loop 45 through a clearance hole 46. The hole 46 is formed at the innermost end of the cable control lever 12, on the side of the pivot screw 16 opposite to the aperture 13 and ratchet lever 22.

A cable connector 48 is located between the closed loop 45 of cable 44 and the cable tension adjustment screw 42. As shown in FIG. 2, the cable connector 48 consists of two parts which are screwed together. One part 50 has a threaded protrusion and the other part 52 has a threaded cavity or bore. Sections of the cable 44 are attached to the respective parts 50 and 52, one section passing through the bore 40 and the other terminating at the clearance hole 46. When the parts 50 and 52 are connected, the cable 44 becomes essentially continuous as shown in FIG. 1.

The angle adjustment section 19 of the cable action instrument 10 is connected to the control end 11 at the threaded end 36 of the control lever handle 14. A universal joint collar 54 is screwed onto the threaded end 36. As shown in FIGS. 1 and 2, a connecting bar 56 with integral ball-shaped ends 58, 60 interacts with universal joint collars 54, 62, respectively, in a ball-and-socket manner.

FIG. 3 shows the control end ball 58 engaged with the indented surface of a plunger 64. The plunger 64 is slidably fitted into a countersunk bore 65. A spring 66 is also located in the bore 65 and surrounds the narrower portion of the plunger 64. The spring 66 exerts a compressive force on the plunger 64 and the ball end 58. The collar 54 holds the ball end 58 in place against the compressive force. A similar structure is present at the opposite end of connecting bar 56 where the ball end 60 engages with the indented surface of the plunger 64. The universal joint collar 62 holds the ball end 60 in place against the compressive force exerted by the spring 66.

The reaction end 17 may consist of a variety of different instrument tips. Shown in FIG. 1 is a scissors tip 68. An instrument tip receptor 70 connects the reaction end 17 to the angle adjustment section 19. A threaded end 72 of the instrument tip receptor 70 is screwed into the second universal joint 62 to form the connection between the reaction end 17 and the angle adjustment section 19. A bore 74 in the instrument tip receptor 70 receives an insertion end 76 of the scissors tip 68. The scissors tip insertion end 76 and the bore 74 fit securely together.

The scissors tip 68 also consists of a stationary blade 78 and a cable activated blade 80 pivotally attached by screw 82. At least one of the two scissors blades 78, 80 is a sharpened blade. Most commonly, if only one blade is a sharpened blade, such will be the cable activated blade 80. The cable 44 is attached to the cable activated blade 80 by forming a loop 83 through a clearance hole 84 on control arm 86. A return spring 88 is attached to the stationary blade 78 by a screw 89 and exerts a force against the cable activated blade 80. As shown in FIG. 1, the force tends to keep the cable activated blade 80 in an open position relative to the stationary blade 78.

The flexible control cable assembly 21 connects the control end 11 to the reaction end 17 of instrument 10. The cable 44 forms a loop 45 through clearance hole 46 of the cable control lever 12. From there, the cable 44 passes through the cable tension adjustment screw 42 and extends to and through bore 96 in the instrument tip receptor 70. A slit 97 intersects the bore 96 and facilitates replacement of the cable 44 when necessary. After passing through the bore 96, the cable 44 is attached to one member 92 of the cable connector 90. A cable loop 83 is attached to the other cable connector member 94 and passes through clearance hole 84 in the cable activated blade 80 of the instrument (scissors) tip 68. The two members, 92, 94 of cable connector 90 are best shown in FIG. 2. Member 94 has a threaded extension which is screwed into a threaded bore in member 92. Between the tension adjustment screw 42 and the instrument tip receptor bore 96, the cable 44 is covered by a flexible sheath 98 which is generally made from a plastic material.

As illustrated by FIG. 2, one of the advantages of the cable action instrument is its ability to be disassembled for easy transport, and more economical storage. When disassembling the instrument for transport or storage it is preferentially broken down into its control end, angle adjustment section and reaction end. The control end is removed from the body of the instrument by unscrewing the cable connector part 50 from the cable connector part 52 then unscrewing the threaded end 36 of the control lever handle 14 from the universal joint collar 54. The angle adjustment section may then be separated from the reaction end by unscrewing the cable connector parts 92, 94 from each other, followed by the separation of the second universal joint collar 62 from the instrument tip receptor 70. Additionally, the instrument tip may be separated from the instrument tip receptor 70 by removal of the tip insertion end 76 from the bore 74. The removal of the instrument tip from the cable action instrument permits its replacement by a different instrument tip with a minimum amount of time and energy expenditure. Further advantages of the ease of disassembly of the instrument are the ability to replace parts without having to replace the entire instrument and the ability to thoroughly clean the instrument before or after use.

A further advantage of the replaceability of parts is that the length of the instrument 10 can be easily increased or decreased by substituting a longer or shorter connecting bar 56 and then substituting a correspondingly longer or shorter cable 44. After disconnecting cable connectors 48 and 90, the cable tension adjustment screw 42 is removed from bore 40 and the cable 44 may be easily removed from bores 40 and 96 by lifting it through slits 45 and 97, respectively. The new cable 44 is slipped into the same bores through the same slits and the cable connectors are reconnected. The connecting bar 56 is just as easily replaced by unscrewing universal joint collars 54 and 62 to remove the old connecting bar 56 and then replacing it with the desired longer or shorter connecting bar by screwing on the attached universal joint collars 54 and 62.

Figure 7:
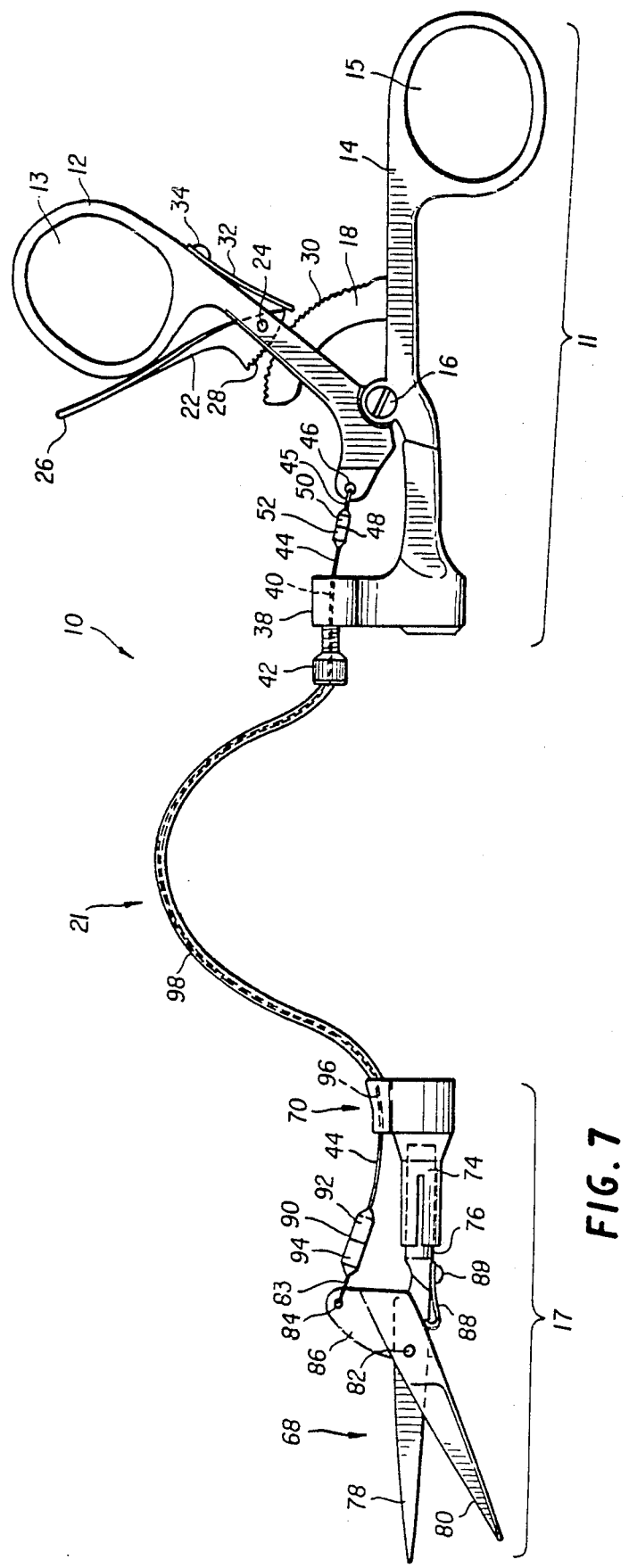
FIG. 7 is a side view of a modified embodiment of the cable action instrument without the angle adjustment section.

As illustrated in FIG. 7, a still further advantage of the disassembly feature of the cable action instrument is the adaptability of the instrument to a modified embodiment which lacks the angle adjustment section 19. With this modified embodiment, the operator of the instrument has even greater ability to reach and operate the reaction end of the instrument 17 at remote and hard-to-reach areas.

As explained above, the cable action instrument 10 is easily converted to the modified embodiment of FIG. 7 by unscrewing universal joint collars 54 and 62 to remove the connecting bar 56. The internal components of the two universal joints would also be removed in the conversion of the cable action instrument 10 to the modified embodiment of FIG. 7. The internal components of the universal joints include the plungers 64 and the springs 66.

When using this modified embodiment, the operator would most commonly use both hands. One hand would operate the control end 11 while the second hand would hold the reaction end 17 in place at the remote area where the desired action is to take place. The actual mechanics by which the modified instrument performs its action are the same as the mechanics for the cable action instrument 10 as set forth below.

When using the cable control instrument with a scissors tip, the operator places his index finger in aperture 13 and his thumb in aperture 15 and applies a squeezing motion with his index finger and thumb to move the cable control lever 12 closer to the control lever handle 14. When using the instrument with the scissors tip, the ratchet lever 22 should remain in an open position such that the lever engaging end 28 is not engaged with the ratchet bar teeth 30. The open position of the ratchet lever 22 permits unhindered squeezing and separating of the cable control lever 12 in relation to the control lever handle 14.

As the cable control lever 12 is squeezed towards the control lever handle 14 a pulling force is exerted on the cable 44. The pulling force is transferred over the length of the cable 44 to the cable activated blade 80. The pulling force causes the cable activated blade 80 to pivot towards a closed position in relation to the stationary blade 78. The force transmitted through the cable 44 to the blade 80 must overcome the opposing force of the return spring 88 which tends to keep the cable activated blade 80 in an open position.

The cable tension adjustment screw 42 is used to align the pivoted position of the cable control lever 12 and the control lever handle 14 with the pivoted position of the cable activated blade 80 and the stationary blade 78. Although any alignment may be made, the preferred alignment is for the two blades 78, 80 to be in a completely closed position when the two levers 12, 14 are in a completely closed position. The actual alignment results for increasing or decreasing the tension of cable 44 by turning the cable tension adjustment screw 42.

Figure 4:
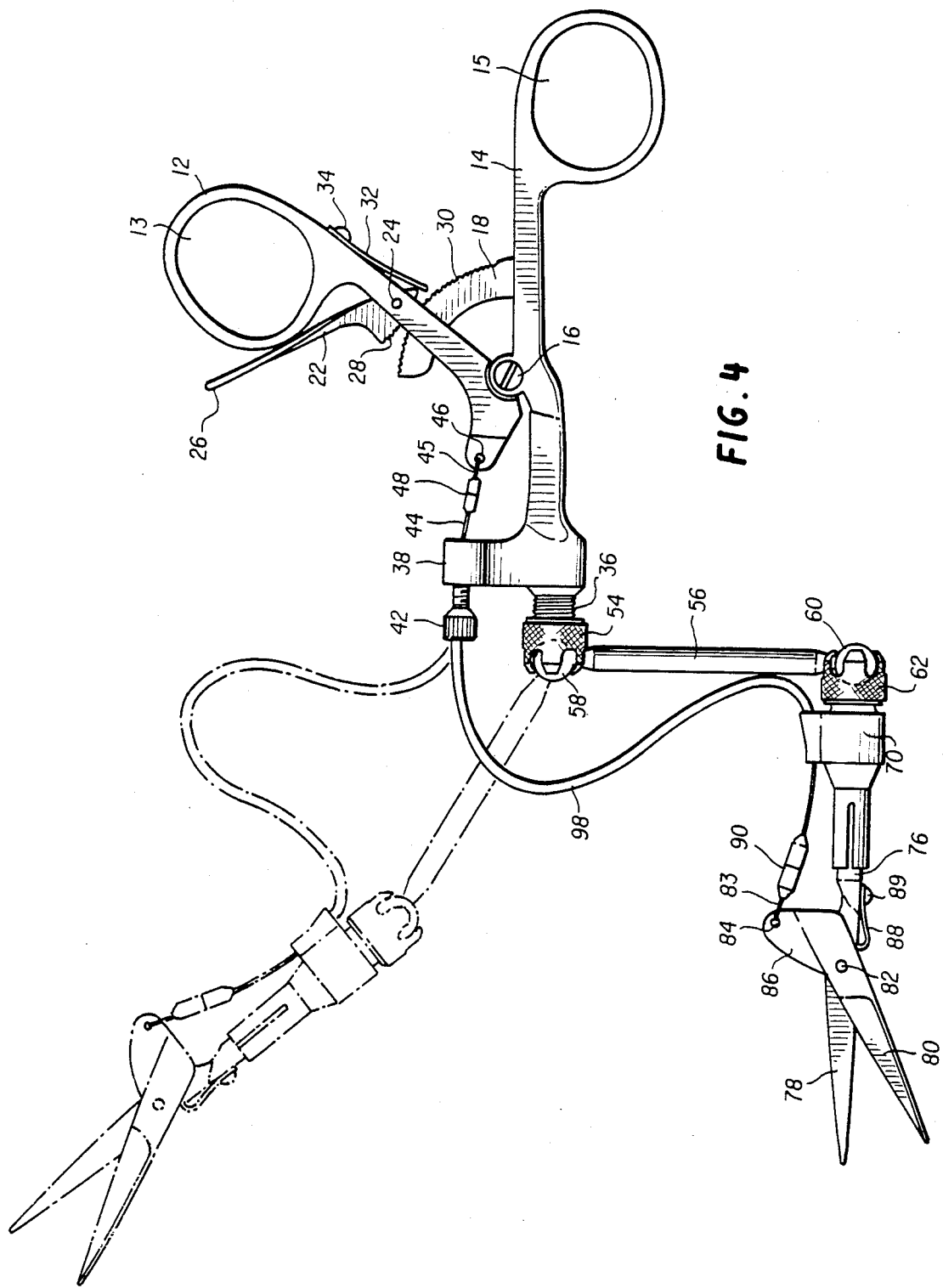
FIG. 4 is a side view of the cable action instrument illustrating different bent positions thereof.

As illustrated by FIG. 4, a major advantage of the cable action instrument 10 is its ability to be positioned into an unlimited number of configurations. The interaction of the two universal joints with the connecting bar 56 allows a full hemispherical range of motion at each joint with the capability of fixing any angle by frictional tightening of the universal joints. The non-permanent angular positioning of the instrument is accomplished by loosening the collar 54 and then adjusting the angle of connecting bar 56. When connecting bar 56 is at the desired angle relative to the control end 11, the collar 54 is tightened so that the angle of connecting bar 56 is temporarily fixed. The same procedure is followed to temporarily fix the angle of connecting bar 56 with respect to the reaction end by loosening collar 62, setting connecting bar 56 at the desired angle and then tightening collar 62. The cable 44 is of sufficient length so as not to hinder the positioning of the instrument. The instrument provides an important advantage to any operator who must perform a function in an area which would be difficult to reach with a conventional instrument. The cable action instrument can be used advantageously by surgeons, dentists and model builders as well as others with similar needs.

FIG. 5 shows the optional forceps instrument tip which may be used with the cable action instrument 10. The forceps tip would be used in place of the scissors tip shown in FIGS. 1 and 2. As shown in FIG. 5, a forceps tip insertion end 100 will fit securely in the bore 74 in the instrument tip receptor 70. The forceps tip consists of a stationary clamp arm 102 which is an integral extension of the tip insertion end 100, and a cable activated clamp arm 104. The cable activated clamp arm 104 is pivotably connected to the stationary clamp arm 102, and a return spring 110 tends to keep the clamp arm 104 in an open position relative to the clamp arm 102. The cable 44 is attached to the control end 106 of the cable activated clamp arm 104 by being looped through a clearance hole 108.

When changing from a scissors tip to a forceps tip, the cable connector 90 must first be disengaged by unscrewing member 94 from member 92. Following the disengagement of the cable connector, the scissors tip 68 may be pulled from the instrument tip receptor 70 thus disengaging the instrument tip insertion end 68 from the bore 74. The forceps tip insertion end 100 may then be securely fit in the bore 74 and the cable connector members 92, 94 screwed back together. The advantages and methods of manipulation of the cable action instrument with a forceps tip are the same as those explained above for the cable action instrument with a scissors tip. The cable activated clamp arm 104 pivots to a less open position when the pulling force on cable 44 overcomes the force exerted by the return spring 110.

The instrument with the forceps tip may also be used as a hemostat by causing the ratchet lever engaging end 28 to interact with the ratchet bar teeth 30. By manipulating the ratchet lever 22 to a closed position before squeezing the cable control lever 12 closer to the control lever handle 14, the ratchet lever engaging end 28 will interact with the ratchet bar teeth 30. This interaction prevents any separation movement of the cable control lever 12 away from the control lever handle 14 unless the ratchet lever 22 is moved back to an open position by pulling the ratchet control end 26. When the instrument is used as a hemostat, the operator may remove his thumb and index finger from the apertures 13 and 15 and cable activated clamp arm 104 will maintain its position relative to stationary clamp arm 102 so long as the ratchet lever engaging 28 and the ratchet bar teeth 30 remain engaged.

Figure 6:
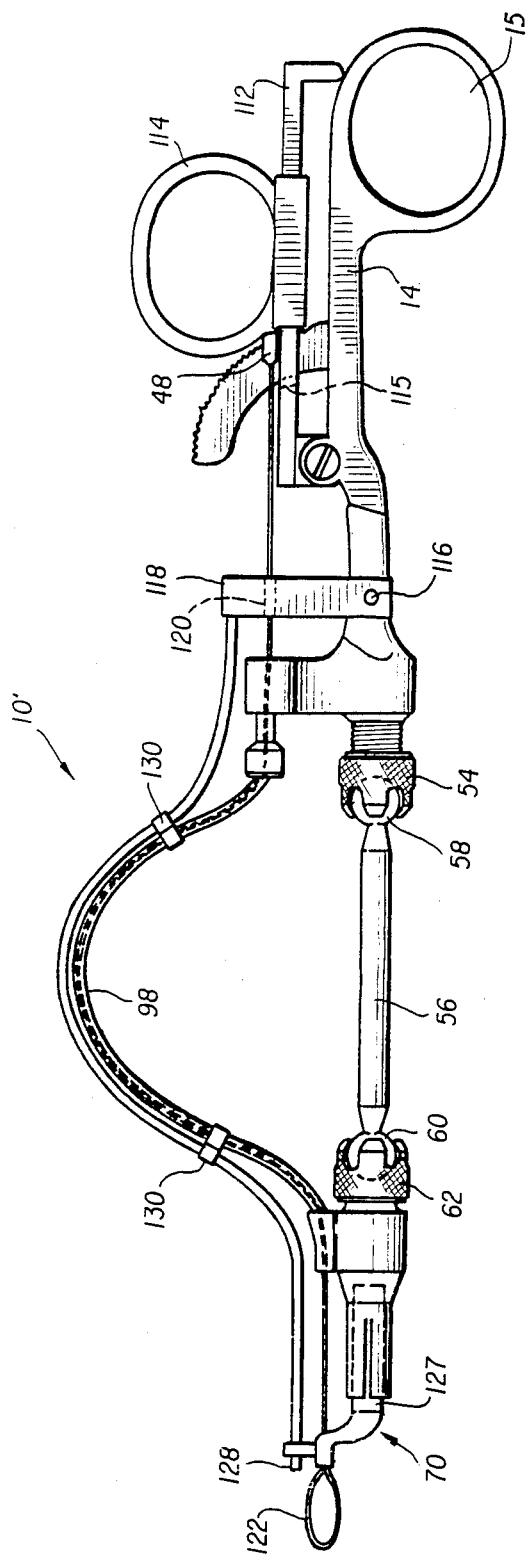
FIG. 6 is a side view of a modified embodiment of the cable action instrument.

FIG. 6 shows a modified cable action instrument 10'. The modified cable action instrument 10' has a different control end 11' and a different reaction end 17'. All parts of the modified cable action instrument 10' which are identical to those of the above described cable action instrument 10 are designated by the same numbers as used above. In place of the cable control lever 12 of the cable action instrument 10, the modified cable action instrument 10' shown in FIG. 6 has a snare slide base 112 and a finger slide 114 mounted thereon. The ratchet bar 18 extends through slot 115 of snare slide base 112 but has no interactive capacity in the modified instrument 10'. The threaded screw 16 secures the snare slide base 112 to the control lever handle 14. A fiber optic light source 118 which consists of a battery source (not shown) and a light source (not shown) is attached to the handle 14 by screw 116. The finger slide 114 is capable of sliding motion on the snare slide base 112 and is attached to the cable 44 by means of cable connector 48 which is directly attached to finger slide 114.

The cable 44 extends from cable connector 48 through a bore 120 in the fiber optic light source 118 and through the cable tension adjustment screw 42 before extending to the instrument tip receptor 70. The cable 44 is covered with the flexible sheath 98 between the cable tension adjustment screw 42 and the instrument tip receptor 70. The cable 44 passes through the bore 96 and is attached to a snare wire 122 by means of the cable connector 90 (not shown). The cable connector 90 and a portion of the snare wire 122 are covered by tubular housing 124. The snare wire tip 126 consists of an insertion end 127 which slides into the bore 74 in the instrument tip receptor 70.

The fiber optic light 128 is in parallel alignment to the cable 44, and is kept in this parallel alignment by means of at least two cable bands 130 spaced along, and wrapped around, the cable 44 and the fiber optic light 128. The fiber optic light 128 illuminates the area in which the snare wire tip 126 cuts small objects or protrusions by tightening the loop of snare wire 122 around the object to be cut. A snare wire type device is often used for the surgical removal of tonsils.

When using the modified cable action instrument 10', the operator places his index finger in aperture 15 and his thumb in finger slide 114. By pulling the finger slide along the length of slide base 112 away from the body of the instrument, the cable 44 is pulled in the same direction and the circumference of snare wire 122 becomes smaller. When the circumference of snare wire 122 has completely closed, the cutting of the object is complete. The instrument is positioned into its desired configuration in the same manner described above by loosening the universal joint collars, setting the connecting bar and then tightening the collars.

The cable action instrument 10 is easily converted to the modified embodiment 10' by changing the reaction end 17 and the control end 11. At the reaction end, the two parts 92, 94 of cable connector 90 are disengaged and the instrument tip insertion end is pulled out of bore 74. The snare wire tip insertion end 127 is then slipped into bore 74 and the cable connector 90 reconnected. At the control end, the cable connector 48 is disengaged by unscrewing parts 50 and 52. Screw 16 is then unscrewed to permit removal of cable control lever 12 and its replacement by slide base 112 with finger slide 114 thereon. Screw 16 is then screwed back into place and cable connector 48 is reconnected. The fiber optic light source 118 may then be attached to control lever handle 14 and the fiber optic light 128 attached to cable sheath 98 by bands 130.

While the invention has been disclosed by reference to the details of various embodiments of the invention, it is understood that this disclosure is intended in an illustrative rather than in a limiting sense, as it is contemplated that modifications will occur to those skilled in the art, within the spirit of the invention and the scope of the appended claims.

What is claimed is:

1. A cable action instrument comprising:
   (a) a control end comprising a cable control lever and a control lever handle pivotally attached thereto;
   (b) a reaction end comprising an instrument tip receptor and an attachable instrument tip;
   (c) an angle adjustment section comprising a connecting bar and two universal joints, said universal joints respectively attached to the control lever handle and the instrument tip receptor, said universal joints being independently adjustable and lockable; and
   (d) a flexible control cable assembly external to the angle adjustment section which transmits a force from the control end to the reaction end, said flexible control cable assembly comprising a cable of sufficient length and proper tension to permit operation of the instrument in a full range of hemispheric positions.

2. The cable action instrument of claim 1 wherein the attachable instrument tip comprises a surgical instrument.

3. The cable action instrument of claim 2 wherein the surgical instrument comprises at least two portions interacting pivotally with one another.

4. The cable action instrument of claim 3 wherein the attachable instrument tip is a scissors.

5. The cable action instrument of claim 2 wherein the attachable instrument tip is a forceps.

6. The cable action instrument of claim 5 wherein the cable control lever and the control lever handle interact by means of a ratchetting mechanism comprising a toothed ratchet bar and a ratchet lever.

7. A cable action instrument comprising:
   (a) a control end comprising a control lever handle, a snare slide base attached thereto, and a finger slide slidably mounted on the snare slide base;

(b) a reaction end comprising an instrument tip receptor and a snare wire;

(c) an angle adjustment section comprising a connecting bar and two universal joints, said universal joints respectively attached to the control lever handle and the instrument tip receptor, said universal joints being independently adjustable and lockable; and (d) a flexible control assembly external to the angle adjustment section which transmits a force from the control end to the reaction end, said flexible control cable assembly comprising a cable of sufficient length and proper tension to permit operation of the instrument in a full range of hemispheric positions.

8. The cable action instrument of claim 7 further comprising a fiber optic light.

* * * * *